(12) United States Patent
Esfandiari

(10) Patent No.: US 12,111,312 B2
(45) Date of Patent: Oct. 8, 2024

(54) CORONAVIRUS IgG/IgM MULTIPLEXED DUAL PATH IMMUNOASSAY DEVICE

(71) Applicant: Chembio Diagnostic Systems, Inc., Medford, NY (US)

(72) Inventor: Javanbakhsh Esfandiari, Stony Brook, NY (US)

(73) Assignee: Chembio Diagnostic Systems, Inc., Medford, NY (US)

( * ) Notice: Subject to any disclaimer, the term of this patent is extended or adjusted under 35 U.S.C. 154(b) by 361 days.

(21) Appl. No.: 17/316,363

(22) Filed: May 10, 2021

(65) Prior Publication Data

US 2021/0349083 A1    Nov. 11, 2021

Related U.S. Application Data

(60) Provisional application No. 63/023,028, filed on May 11, 2020.

(51) Int. Cl.
*G01N 33/543* (2006.01)
*G01N 33/569* (2006.01)

(52) U.S. Cl.
CPC . *G01N 33/54366* (2013.01); *G01N 33/56983* (2013.01); *G01N 2333/165* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 7,189,522 B2 | 3/2007 | Esfandiari | |
| 7,682,801 B2 | 3/2010 | Esfandiari | |
| 7,879,597 B2 | 2/2011 | Esfandiari | |
| 8,507,259 B2* | 8/2013 | Esfandiari | G01N 33/5695 435/7.1 |
| 8,877,450 B2* | 11/2014 | Esfandiari | G01N 33/56988 435/7.1 |
| 9,784,734 B2 | 10/2017 | Esfandiari | |
| 9,791,437 B2 | 10/2017 | Egan et al. | |
| 9,885,710 B2 | 2/2018 | Esfandiari | |
| 10,473,655 B2 | 11/2019 | Esfandiari | |
| 10,598,657 B2 | 3/2020 | Esfandiari | |
| 10,690,667 B2 | 6/2020 | Esfandiari | |
| 10,976,315 B2 | 4/2021 | Esfandiari | |
| 2011/0151584 A1 | 6/2011 | Esfandiari | |
| 2012/0208299 A1 | 8/2012 | Esfandiari | |
| 2019/0125859 A1 | 5/2019 | Palese et al. | |

FOREIGN PATENT DOCUMENTS

| | | |
|---|---|---|
| EP | 2023142 A1 | 2/2009 |
| WO | 2011/103074 A1 | 8/2011 |

OTHER PUBLICATIONS

In Vitro Diagnostic Assays for COVID-19: Recent Advances and Emerging Trends. VASHIST SK., Diagnostics, Apr. 5, 2020, vol. 10, No. 4, article 202 (pp. 1-7).
PCT Search Report and Written Opinion dated Sep. 9, 2021 of International Application No. PCT/US21/031552.
"Antibody Persistence through 6 Months after the second Dose of mRNA-1273 Vaccine for Covid-19", The New England Journal of Medicine, Apr. 6, 2021, DOI: 10.1056/NEJMc2103916.
"Comparison of Four Clinical Specimen Types for Detection of Influenza A and B Viruses by Optical Immunoassay (FLU OIA Test) and Cell Culture Methods", Kristi A. Covalciuc et al., Journal of Clinical Microbiology, DOI: 10.1128/JCM.37.12.3971-3974; 1999.
"COVID-19 IgG/IgM Rapid Test", Published Feb. 9, 2020, available at https://primahometest.com/en/covid-19_serological_test.
"Fluorescent Antibody Techniques", Microbiology, downloaded Apr. 12, 21; available at https://courses.lumenlearning.com/microbiology/chapter/fluorescent-antibody-techniques/.
"Interpreting Diagnostic Tests for SARS-COV-2", Sundararaj Stanleyraj et al., JAMA, Jun. 9, 2020, vol. 323, No. 22, pp. 2249-2251.
"Nasopharyngeal and Serological Anti SARS-COV-2 IgG/IgA Responses in Covid-19 Patients", medRxiv preprint doi: https://doi.org/10.1101/2021.01.13.20249038; Jan. 15, 2021.
"Orthogonal immunoassays for IgG Antibodiesto SARS-COV-2 antigens reveal that immune response lasts beyond 4 mo post illness onset", Varun Sasisekharan et al., PNAS 2021 vol. 118 No. 5; e2021615118.
"Persistence of serum and saliva antibody responses to SARS-COV-2 spike antigens in COVID 19 patients", B. Isho et al., Sci. Immunol. 10.1126/sciimmunol.abe5511 (2020).

(Continued)

*Primary Examiner* — Nicole Kinsey White
(74) *Attorney, Agent, or Firm* — Gordon & Jacobson, P.C.

(57) ABSTRACT

Test cells with first and second sorbent materials defining a first flow path for a solution, a second flow path distinct from the first flow path for a sample, and a test site with immobilized antigens or antibodies or other ligand-binding molecules located at the junction of the sorbent materials for identifying one or more ligands. In one embodiment, a single highly sensitive immunoassay device is provided that detects the presence in a body fluid sample of two or more COVID-19 (Coronavirus disease 2019) antibodies including immunoglobulin M (IgM) and/or immunoglobulin G (IgG) antibodies to nucleocapsid protein (NP) and spike protein receptor binding domain (RBD), and optionally spike protein S1 subunit (S1) COVID-19 virus antigens. The immunoassay device is sensitive in detecting early infection using IgM antibody detection and continuing infection using IgG antibody detection. Additionally, successful inoculation is distinguished from infection after inoculation by comparing NP and RBD results.

15 Claims, 11 Drawing Sheets

(56) References Cited

OTHER PUBLICATIONS

"Quantitative Influenza Antibody (Nasal or Throat Swab)", University of Rochester Medical Center Health Encyclopedia, downloaded Apr. 12, 2021, available at https://www.urmc.rochester.edu/encyclopedia/content.aspx?contenttypeid=167&contentid=quantitative_influenza_antibody.

"SARS-COV-2 IgG/IgM Rapid Test as a Diagnostic Tool in Hospitalized Patients and Healthcare Workers, at a large Teaching Hospital in northern Italy, during the 2020 COVID-19 Pandemic", Diana Canetti et al.; New Microbiologica, 43, 4, 161-165, 2020, ISSN 1121-7138.

"Systemic and mucosal antibody secretion specific to SARS-COV-2 during mild versus severe COVID-19", bioRxiv preprint doi: https://doi.org/10.1101/2020.05.21.108308; May 23, 2020.

EP Supplemental Search Report and Written Opinion dated Jul. 4, 2024 of Application No. 21 803 753.9.

* cited by examiner

Interpreting the Test Results

DO NOT ATTEMPT TO INTERPRET RESULTS VISUALLY. ALWAYS USE THE DPP® MICRO READER II TO OBTAIN RESULTS.

| | REACTIVE | NON-REACTIVE |
|---|---|---|
| Test Line 1: Nucleocapsid Protein | NP IgM ≥25 — An IgM Reactive test result means that IgM antibodies to that antigen has been detected in the specimen.<br>NP IgG ≥25 — An IgG Reactive test result means that that IgG antibody has been detected in the specimen.<br>A reader Test Line numerical result ≥25 indicates a REACTIVE Test Result | NP IgM <24 — An IgM Non-Reactive test result means that IgM antibodies to that antigen have NOT been detected in the specimen.<br>NP IgG <24 — An IgG Non-Reactive test result means that IgG antibodies to that antigen have NOT been detected in the specimen.<br>A reader Test Line numerical result <25 indicates a NON-REACTIVE Test Result |
| Test Line 2: Spike Protein S1 Subunit | S1 IgM ≥25 — An IgM Reactive test result means that IgM antibodies to that antigen has been detected in the specimen.<br>S1 IgG ≥25 — An IgG Reactive test result means that that IgG antibody has been detected in the specimen.<br>A reader Test Line numerical result ≥25 indicates a REACTIVE Test Result | S1 IgM <24 — An IgM Non-Reactive test result means that IgM antibodies to that antigen have NOT been detected in the specimen.<br>S1 IgG <24 — An IgG Non-Reactive test result means that IgG antibodies to that antigen have NOT been detected in the specimen.<br>A reader Test Line numerical result <25 indicates a NON-REACTIVE Test Result |
| Test Line 3: Spike Protein Receptor Binding Domain | RBD IgM ≥25 — An IgM Reactive test result means that IgM antibodies to that antigen has been detected in the specimen.<br>RBD IgG ≥25 — An IgG Reactive test result means that that IgG antibody has been detected in the specimen.<br>A reader Test Line numerical result ≥25 indicates a REACTIVE Test Result | RBD IgM <24 — An IgM Non-Reactive test result means that IgM antibodies to that antigen have NOT been detected in the specimen.<br>RBD IgG <24 — An IgG Non-Reactive test result means that IgG antibodies to that antigen have NOT been detected in the specimen.<br>A reader Test Line numerical result <25 indicates a NON-REACTIVE Test Result |
| INV | An INVALID test cannot be interpreted. Test should be repeated with a new test device. | |

Ordering Information:
Cat No.      Description
00-0000-0    DPP® COVID-19 IgM/IgG Confirmatory System
00-0000-0    DPP® Micro Reader II for Immunostatus Confirmatory System
             DPP® COVID-19 IgM/IgG Confirmatory System

CHEMBIO
DIAGNOSTIC SYSTEMS, INC.

FIG. 5

| Sample ID | PCR positive COVID-19 Data | DPP COVID-19 IgM/IgG Immunostatus Confirmatory System ||||||||| 
| | | NP-Rec Ag | S1-Rec-Ag | RBD-rec-Ag | NP-Rec Ag | S1-Rec-Ag | RBD-rec-Ag | Results interpretation |||
| | | IgM Pos ≥25 ||| IgG Pos ≥25 ||| IgM | IgG | Total Antibody IgM/IgG |
| | | DPP Micro Reader II Value ||| DPP Micro Reader II Value |||  |  |  |
| Total positive result | 56 | 41 | 34 | 43 | 50 | 41 | 49 | 49 | 56 | 56 |
| Total Negative result | 18 | 33 | 40 | 31 | 24 | 33 | 25 | 25 | 18 | 18 |
| Total samples | 74 | 74 | 74 | 74 | 74 | 74 | 74 | 74 | 74 | 74 |
| Total sensitivity | 100% | 73% | 60% | 77% | 89% | 73% | 88% | 88% | 100% | 100% |

FIG. 6

CORONAVIRUS IgG/IgM MULTIPLEXED DUAL PATH IMMUNOASSAY DEVICE

This application claims priority from U.S. Ser. No. 63/023,028 filed on May 11, 2020. This application relates to co-owned U.S. Pat. Nos. 7,189,522, 7,682,801, 7,879,597, 8,507,259, 8,877,450, 9,784,734, 9,885,710, 10,473,655, 10,598,657, 10,690,667, and 10,976,315 all of which are hereby incorporated by reference herein in their entireties.

BACKGROUND OF THE INVENTION

1. Field of the Invention

This disclosure relates broadly to immunoassay devices and the methods for their use. More particularly, this disclosure relates to chromatographic rapid test strips for detection of one or more ligands in a body fluid. This disclosure has particular application to the testing for the presence in a body fluid sample of COVID-19 (SARS-Cov-2) IgM, and IgG antibodies including antibodies to nucleocapsid proteins (NP), spike protein S1 subunits (S1), and spike protein receptor binding domain (RBD), although it is not limited thereto.

2. State of the Art

Many types of ligand-receptor assays have been used to detect the presence of various substances, often generally called ligands, in body fluids such as blood, urine, or saliva. These assays involve antigen antibody reactions, synthetic conjugates comprising radioactive, enzymatic, fluorescent, or visually observable polystyrene or metal sol tags, and specially designed reactor chambers. In all these assays, there is a receptor, e.g., an antibody, which is specific for the selected ligand or antigen, and a means for detecting the presence, and in some cases the amount, of the ligand-receptor reaction product. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

Even the qualitative assays must be very sensitive because of the often small concentration of the ligand of interest in the test fluid. False positives can also be troublesome, particularly with agglutination and other rapid detection methods such as dipstick and color change tests. Because of these problems, so-called "sandwich" assays and other sensitive detection mechanisms which use metal sols or other types of colored particles have been developed.

In a "sandwich" assay, a target analyte such as an antigen is "sandwiched" between a labeled antibody and an antibody immobilized onto a solid support. The assay is read by observing the presence and/or amount of bound antigen-labeled antibody complex. In a "competition" immunoassay, antibody bound to a solid surface is contacted with a sample containing an unknown quantity of antigen analyte and with labeled antigen of the same type. The amount of labeled antigen bound on the solid surface is then determined to provide an indirect measure of the amount of antigen analyte in the sample.

Because these and other assays can detect both antibodies and antigens, they are generally referred to as immunochemical ligand-receptor assays or simply immunoassays.

Solid phase immunoassay devices, whether of the sandwich or competition type, provide sensitive detection of an analyte in a biological fluid sample such as blood, urine, or saliva. Solid phase immunoassay devices incorporate a solid support to which one member of a ligand-receptor pair, usually an antibody, antigen, or hapten, is bound. Common early forms of solid supports were plates, tubes, or beads of polystyrene which were well known from the fields of radioimmunoassay and enzyme immunoassay. In the last decade, a number of porous materials such as nylon, nitrocellulose, cellulose acetate, glass fibers, and other porous polymers have been employed as solid supports.

SUMMARY

A rapid detection immunoassay device is disclosed. The rapid detection immunoassay device is simple to use and provides accurate results.

In embodiments, the rapid immunoassay devices do not require migration of analytes along the same path as conjugate carrying buffer solutions.

In embodiments, the rapid immunoassay devices can use either a dry or liquid conjugate system.

The disclosed rapid immunoassay devices are highly sensitive and provide accurate results while using small sample volumes.

In embodiments, the highly sensitive immunoassay devices are useful with different types of body fluids.

In embodiments, a single highly sensitive immunoassay device is provided that detects the presence in a body fluid sample of at least two antibodies of a single virus (e.g., COVID-19—also known as Severe Acute Respiratory Syndrome Coronavirus-2 or SARS-Cov-2).

In embodiments, a single highly sensitive immunoassay device is provided that detects the presence in a body fluid sample of immunoglobulin M (IgM) antibodies of a single virus (e.g., COVID-19).

In embodiments, a single highly sensitive immunoassay device is provided that detects the presence in a body fluid sample of immunoglobulin G (IgG) antibodies of a single virus (e.g., COVID-19).

In embodiments, a single highly sensitive immunoassay device is provided that detects the presence in a body fluid sample of two COVID-19 antibodies including immunoglobulin M (IgM) and immunoglobulin G (IgG) antibodies to nucleocapsid proteins (NP), spike protein S1 subunits (S1), and spike protein receptor binding domain (RBD) of the COVID-19 virus.

In embodiments, both dry and liquid conjugate immunoassay device systems are provided. The systems include test cells with a first sorbent material having a first location for receiving a buffer solution (in the case of a dry conjugate system) or a conjugate solution (in the case of a liquid conjugate system) with the first sorbent material defining a first horizontal flow path, a second sorbent material having a second location for receiving a sample with the second sorbent material defining a second horizontal flow path distinct from the first flow path, and test spots (e.g., lines) or test sites with immobilized antigens or antibodies or other ligand binding molecules such as aptamers, nucleic acids, etc. located in a test zone at a junction of the first and second sorbent materials. For purposes herein, the term "distinct" when used in conjunction with the words "flow path" or "migration path" shall be understood to mean "not in fluid communication except via a test zone".

Where the test cell is provided in a housing, the housing is provided with a first opening adjacent the first location and a second opening adjacent the second location. A viewing window is provided in the housing above the test line.

In embodiments, the first sorbent material and second sorbent material are separate pieces having different pore sizes which overlie one another and the test line is printed on one or both of the sorbent materials at the junction. The systems may also include a control line or site which may be seen from the viewing window.

According to one set of embodiments, the sorbent materials (and optionally the housing in which the materials are provided) are laid out in a T shape, where the first location for receiving the buffer or buffer-conjugate solution is located near one end of the top bar of the T, the second location for receiving the sample is located near the end of the stem of the T, and the sorbent materials overlie each other at the intersection. Of course, the sorbent materials may be laid out in other configurations, and the housing may take other shapes, such as rectangular, square, irregular, etc. regardless of the manner in which the sorbent materials are arranged.

In one embodiment, the materials, thicknesses and lengths of the first and second sorbent materials are chosen to adjust the timing regarding the liquid sample and liquid buffer reaching the first site.

In the dry conjugate system, a dry conjugate is provided between the first opening and the test site. The conjugate is supported on or within the sorbent material such that when a buffer is added in the first opening, the sorbent material wicks the buffer to the conjugate which is then carried by the buffer to the test site. In the liquid conjugate system of the invention, a buffer-conjugate liquid subsystem is provided and applied to the first opening. The sorbent material then wicks the buffer-conjugate subsystem to the test site.

According to one method, a system is provided which includes a test cell having a first sorbent material having a first location for receiving a buffer solution (in the case of a dry conjugate system) or a conjugate solution (in the case of a liquid conjugate system) with the first sorbent material defining a first horizontal flow path, a second sorbent material having a second location for receiving a sample with the second sorbent material defining a second horizontal flow path distinct from the first flow path, and test lines or test sites with immobilized antigens or antibodies or other ligand binding molecules such as aptamers, nucleic acids, etc. located in a test zone at a junction of the first and second sorbent materials. If desired, a housing is also provided having a first opening for receiving the buffer or conjugate solution, a second opening for receiving a sample, and a viewing window above the test line. A sample of interest is provided to the second opening or location and does not immediately wet the test site as it is removed from the test site. After a desired amount of time (which permits the sample to migrate down to the test site), a liquid such as a buffer solution is added to the first opening or location. If the sorbent material is supporting a conjugate (i.e., in a dry conjugate system), the liquid is preferably simply a buffer solution. If the sorbent material is not supporting a conjugate (i.e., in a liquid conjugate system), the liquid is preferably a buffer-conjugate liquid subsystem. In any event, after sufficient time to permit the conjugate to migrate to the test sites (and control site if provided), the test sites (and control site if provided) is inspected in order to determine whether the sample is "positive" or not.

It will be appreciated that the system of the disclosure can be used in conjunction with different types of samples such as blood, nasal mucus, urine, saliva, and feces, and can be used to test for the presence of any ligand. Where blood, saliva, nasal mucus or feces is to be provided, the blood, saliva, nasal mucus or feces may be diluted or mixed with buffer prior to being added through the second hole. Alternatively, in some cases, the sample may be added through the hole and then a diluent may be added through the same hole.

In some embodiments, a fourth generation rapid detection immunoassay device is provided where the analytes migrate along different paths than conjugate-carrying buffer solutions. The systems include test cells having a first buffer-receiving location which receives a buffer solution and a first sorbent material defining a first horizontal flow path for the first buffer solution, a second sorbent material defining a second horizontal flow path distinct from said first horizontal flow path for the same or a different buffer solution provided to the first buffer-receiving location or to a second buffer-receiving location, a third sorbent material defining a third horizontal flow path for a sample provided at a sample-receiving location, said third horizontal flow path being distinct from said first and second horizontal flow paths, a fourth flow path for the sample provided at the sample-receiving location, said fourth horizontal flow path being distinct from said first, second, and third horizontal flow paths, one or more first test lines or test sites with one of immobilized antigens or antibodies located in a first test zone at a junction of the first and third sorbent materials, and one or more second test lines or test sites with the other of the immobilized antigens or antibodies located in a second test zone at a junction of the second and fourth sorbent materials. For purposes herein, the term "distinct" when used in conjunction with the words "flow path" or "migration path" shall be understood to mean "not in fluid communication except either (i) via a test zone, or (ii) at a buffer receiving or sample receiving location".

In one embodiment of the fourth generation devices, the third sorbent material and fourth sorbent material are separate pieces which are coupled to a single sample receiving pad. Alternatively, if desired, the third and fourth sorbent materials can be integral with each other. Also, in embodiments, the first sorbent material and second sorbent material are separate pieces which may be coupled to the same buffer receiving pads or to two different buffer receiving pads. However, if desired, in an embodiment where a single buffer receiving pad is utilized, the first and second sorbent materials can be integral with each other. In embodiments, a control line or site is provided adjacent each test zone.

In the dry conjugate fourth generation system, a first dry conjugate is provided between the first opening and the first test zone. The first dry conjugate is supported on or within the first sorbent material such that when a buffer is added in the first opening, the first sorbent material wicks the buffer to the first conjugate which is then carried by the buffer to the first test zone. A second dry conjugate is likewise supported on or within the second sorbent material such that when buffer is added in the first or second opening (if provided), the second sorbent material wicks the buffer to the second conjugate which is then carried by the buffer to the second test zone. In the liquid conjugate fourth generation system, a first buffer-conjugate liquid subsystem is provided and applied to the first opening. The first sorbent material then wicks the first buffer-conjugate subsystem to the first test zone. A second buffer-conjugate liquid subsystem is provided and applied to the second opening. The second sorbent material then wicks the second buffer-conjugate subsystem to the second test zone.

According to one embodiment, a COVID-19 test device has at least two sorbent strips with a first sorbent strip receiving a sample and a second sorbent strip on which conjugated particles are located receiving a buffer. The COVID-19 test device includes a test zone with at least two separate test spots (lines): a first test line having COVID-19 nucleocapsid protein (NP) antigen, and a second test line having COVID-19 spike protein receptor binding domain (RBD) antigen or a COVID-19 spike protein S1 subunit (S1) antigen. If desired, where the first two test lines include the NP and RBD antigen, a third test line having COVID-19 spike protein S1 subunit (S1) antigen may be provided. The provided test device gives the surprising results that antibodies to two or three separate proteins (e.g., NP and RBD, or NP and S1, or NP, RBD and S1) of a single virus can be separately, accurately and specifically detected at the test lines in one test zone of a single test unit. Further, if desired, a depletion zone of, e.g., anti-human IgM antibodies conjugated to particles may be provided in or on the sorbent strip that receives the sample. In this manner, IgM antibodies in the sample will be depleted, and only IgG antibodies to those separate COVID-19 proteins will be separately, accurately and specifically detected at the test lines.

According to another embodiment, a COVID-19 test device has at least two sorbent strips having respectively anti-human IgM antibodies conjugated to particles and protein A conjugated to particles, each for receiving a solution such as a buffer solution, and at least one sorbent strip for the sample which intersects the two sorbent strips at separate test zones; a first depletion zone with a conjugate of a latex particle with antigen or anti-human IgG, and if needed a second depletion zone with a conjugate of a latex particle with antigen on the sorbent strip which receives the sample on opposite sides of the location receiving the sample; and multiple test lines in each of the separate test zones. On the other hand, according to aspects, the COVID-19 test device includes specific COVID-19 nucleocapsid protein (NP) antigen, specific COVID-19 spike protein S1 subunit (S1) antigen, and specific COVID-19 spike protein receptor binding domain (RBD) antigen as three separate test lines in each of the test zones which gives the surprising results that IgG antibodies to three separate proteins of a single virus, COVID-19, (i.e., NP, S1, and RBD) can be separately, accurately and specifically detected at the test lines in one test zone of a single test unit, and IgM antibodies to those three separate COVID-19 proteins can be separately, accurately and specifically detected at the test lines in another test zone of the same test unit, using a single small (blood) sample.

Additional objects and advantages will become apparent to those skilled in the art upon reference to the detailed description taken in conjunction with the provided figures.

BRIEF DESCRIPTION OF THE DRAWINGS

FIG. 5 is a chart of possible results provided by the reader of FIG. 3.

FIG. 6 is a chart of actual test results from samples run through the test kit system of FIG. 3.

DETAILED DESCRIPTION OF THE PREFERRED EMBODIMENTS

Figure 1:
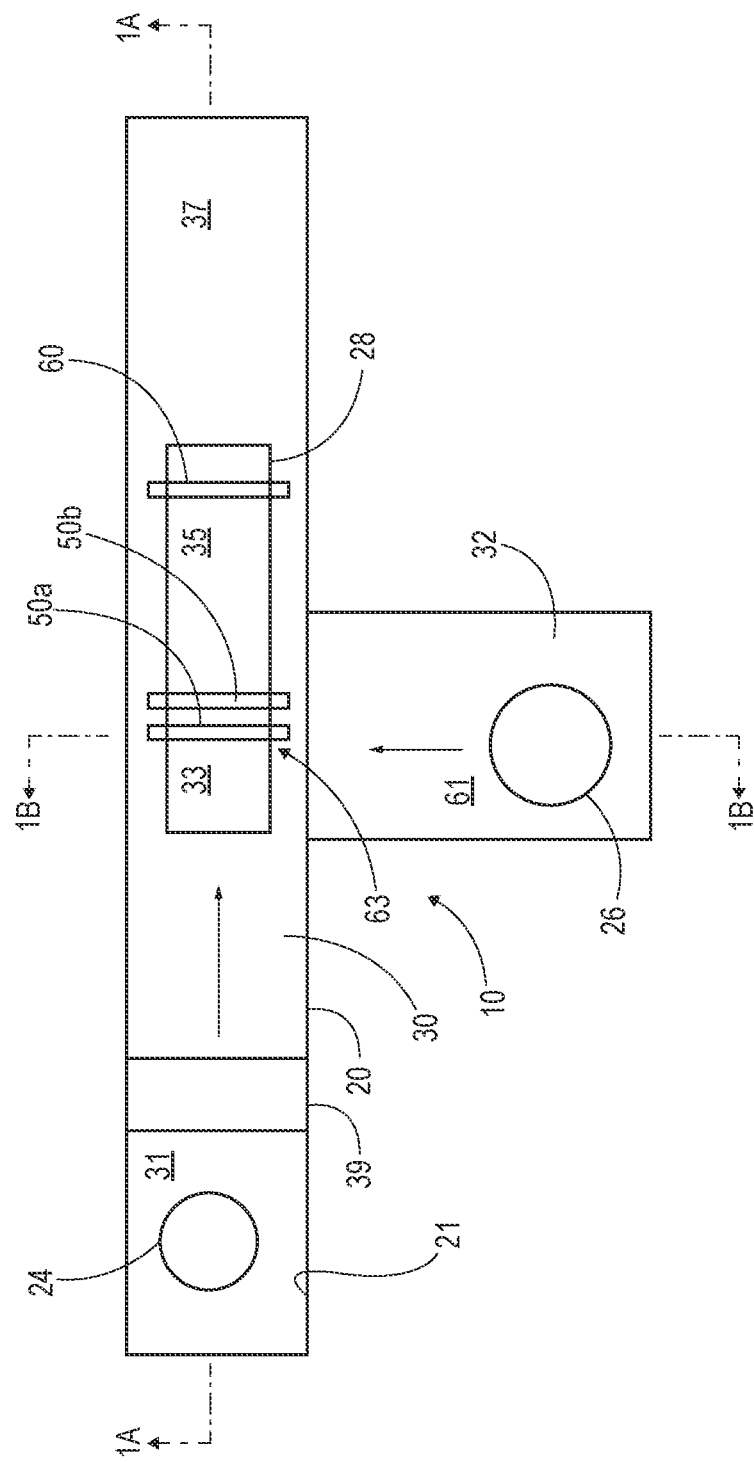
FIG. 1 is a top schematic view of a first embodiment.
Figure 1A:
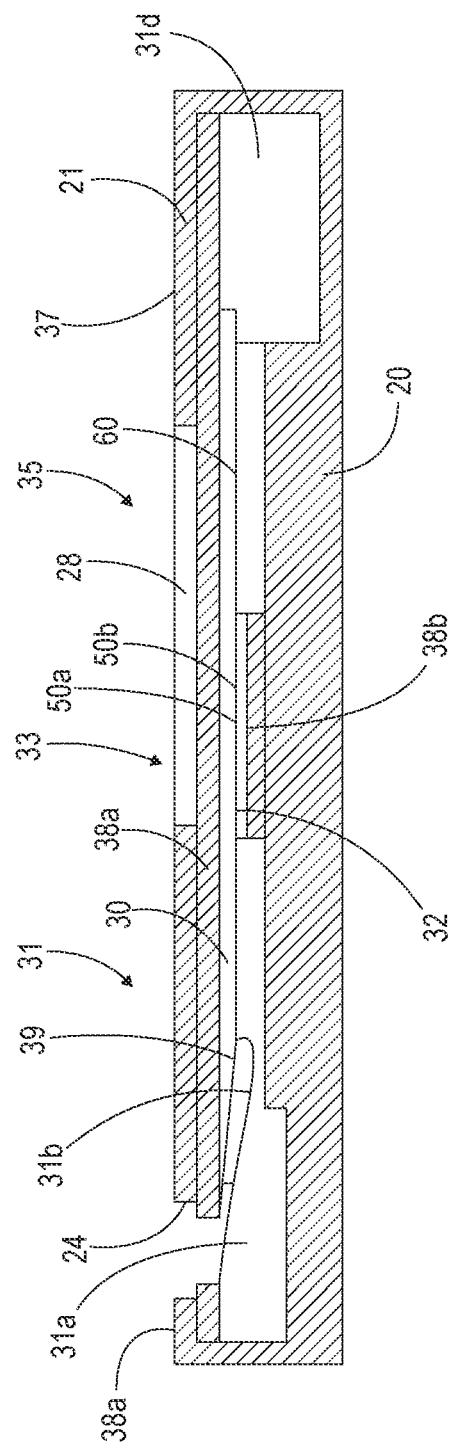
FIG. 1A is a cross-sectional view taken along line 1A-1A of FIG. 1.
Figure 1B:
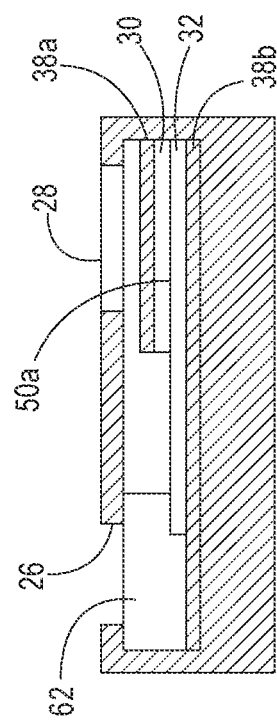
FIG. 1B is a cross-sectional view taken along line 1B-1B of FIG. 1.

Turning now to FIGS. 1, 1A and 1B, an immunoassay device test cell 10 is provided and includes: a T-shaped housing 20 having a top wall 21 defining first and second holes 24, 26, and a window 28; and first and second sorbent or bibulous materials 30, 32 defining perpendicular horizontal flow paths in the housing. The first sorbent material 30 includes at least two and preferably three or four zones and may be made from a plurality of materials. A first zone 31 (sometimes called a filter zone) is located at the first hole 24 and extends to a second zone 33 (sometimes called a test zone) which is located at the junction of the "T". The first zone 31 preferably includes a filter 31a, a pad 31b on or in which a conjugate 39 having desired antigens or antibodies with attached colored markers is deposited and immobilized, and a first portion of a thin membrane or sorbent or bibulous material 30 typically made from nitrocellulose with a plastic backing (not shown). The first zone 31 is adapted to receive a buffer solution, to cause the buffer solution to contact the conjugate, thereby mobilizing the conjugate, and to wick the conjugate-carrying buffer solution to the second zone 33. The second (test) zone 33 includes a second portion of the thin membrane 30 which is preferably printed with a test lines 50a, 50b having immobilized antigens on the membrane as is well known in the art. The test lines 50a, 50b may be seen through the window 28 of clear plastic provided in the housing. An optional third zone 35 (sometimes called a control zone) which includes a third portion of the thin membrane 30 may also be printed with a control line 60 typically containing antibodies to the conjugate antigens (or in some cases antibodies which will bind to conjugate antibodies, or even antigens which will bind to conjugate antibodies) as is well known in the art. Where the third zone 35 is provided, window 28 extends above the control line 60. If desired, an optional fourth zone 37 (sometimes called a reservoir zone) may be provided as a wicking reservoir as is also well known in the art. The fourth zone 37 includes a relatively thicker absorbent paper 31d. Preferably overlying all the zones is a thin, preferably transparent plastic film or card 38a having an adhesive which keeps the sorbent materials in place. The card 38a may be cut with an opening at hole 24 so that it does not block liquid access to the hole 24.

The second sorbent material 32 may also be made from a plurality of materials and preferably includes two zones 61, 63. The first zone 61 (sometimes called a filter zone) includes a filter or pad 62 and a first portion of a thin membrane or sorbent or bibulous material 32 typically made from nitrocellulose with a backing (not shown). The first zone 61 is located at the second hole 26 and extends to the second zone 63. The second zone 63 includes a second portion of the thin membrane 32 which is in contact with the second zone 33 of the first sorbent material 30. As is seen in FIGS. 1A and 1B, the first sorbent material 30 overlies the second sorbent material 32 such that the membranes are in contact with each other (as opposed to the backings contacting the membranes or each other), and such that the test lines 50a, 50b are effectively located between the membranes. Thus, test lines 50a, 50b could be printed on the second zone 63 of the second sorbent material 32 instead of, or in addition to the second zone 33 of the first sorbent material 30. If desired, a thin plastic film or card 38b having an adhesive which keeps the second sorbent material in place may be utilized.

Where standard-type nitrocellulose strips with a backing are utilized as the first and second membranes, it is desirable for the membranes to have different pore sizes. For example, and as discussed in more detail hereinafter, if membrane 31 (for the conjugate migration) has a 3 μ pore size, and membrane 32 (for the sample migration) has a 15 μ pore size, sample applied to membrane 32 will tend to migrate and stay in the sample membrane 32 and will tend not to migrate into the conjugate membrane 31.

The immunoassay of FIG. 1 is preferably utilized as follows. First, a sample (not shown—and constituting blood, nasal mucus, urine, saliva, feces, or any other bodily fluid or excretion that could contain antibodies) possibly containing antibodies (or antigens) is provided to the second opening or hole 26 and allowed to migrate through the second sorbent material 32 to its second zone 63 which is contact with the second zone 33 of the first sorbent material 30. Optionally, after providing the sample to hole 26, a preferably measured amount of liquid such as a buffer solution may be added to hole 26 to help in the migration of the sample. Regardless, the sample reaches the test lines 50a, 50b which are printed atop the second zone 33 of the first sorbent material or infused therein. After a desired amount of time, by which time the antibodies in the sample (if present) will have had an opportunity to bind to the antigens immobilized at the test lines 50a, 50b, a preferably measured amount of liquid such as a buffer solution (not shown) is added to the first opening 24. After another period of time, sufficient to permit the conjugate to migrate to the test lines 50a, 50b (and control site 60 if provided), the test lines 50a, 50b (and control site 60 if provided) are inspected via window 28 in order to determine whether the sample is "positive" or not. Typically, a "positive" test indicating the presence of the antibody in the sample is obtained when one or both of the test lines 50a, 50b and the control site 60 show lines of color. A "negative" test indicating the lack of the presence of the antibody (or antigen) in the sample is obtained when only the control site 60 shows a line of color.

The methods of use may be expedited by providing the housing with numbering and/or lettering to indicate that hole 26 is for receiving the sample (and optionally some buffer) and is to be used first, and that hole 24 is for receiving the buffer solution and is to be used second.

Those skilled in the art will appreciate that the immunoassay 10 functions as follows. Because the test lines 50a, 50b are provided with antigens immobilized on a membrane, if the test sample contains antibodies to the antigens, the antibodies will bind themselves to the antigens at the test line. Thereafter, when the conjugate 39 containing an antigen for the antibody coupled to a colored marker is caused to migrate to the test line, if the test sample contains the antibodies which are now held at one or both of the test lines 50a, 50b, the antigen of the conjugate will bind itself to the antibodies and the colored marker will cause a colored line to appear at one or both of the test sites 50a, 50b. If the test sample does not contain antibodies, the conjugate will not have the antibodies to bind to at the test lines, and no colored line(s) will appear at the test site(s). On the other hand, because the control line 60 is provided with antibodies, the antigens of the conjugate will always bind to the antibodies in the control line 60, thereby causing a colored line to appear at the control site 60 if the conjugate reaches the control site 60. Thus, if sufficient buffer solution is provided to the test cell, a colored line should always appear at the control site 60, thereby providing a control for the test.

In one embodiment, the test lines 50a, 50b are antigens that will respectively specifically capture two different antibodies of a single virus. For example, the antigens may specifically capture two different proteins of COVID-19 virus antibodies such as the NP and RBD proteins, or the NP and S1 proteins, or the RBD and S1 proteins, etc. In embodiments, and as described in more detail hereinafter, the antigens may specifically capture two different proteins of COVID-19 virus IgG antibodies or two different proteins of COVID-19 virus IgM antibodies. That the different proteins of a single virus may be captured and detected with high sensitivity and specificity is a surprising result, and the information that may be gleaned from those results is also surprising. For example, as described in more detail hereinafter, a test showing a lack of antibodies to the NP protein but the presence of antibodies to the RBD and/or S1 proteins can show that the subject has received a vaccination, whereas a test showing the presence of antibodies to the NP protein may show an ongoing COVID-19 viral infection.

Figure 2:
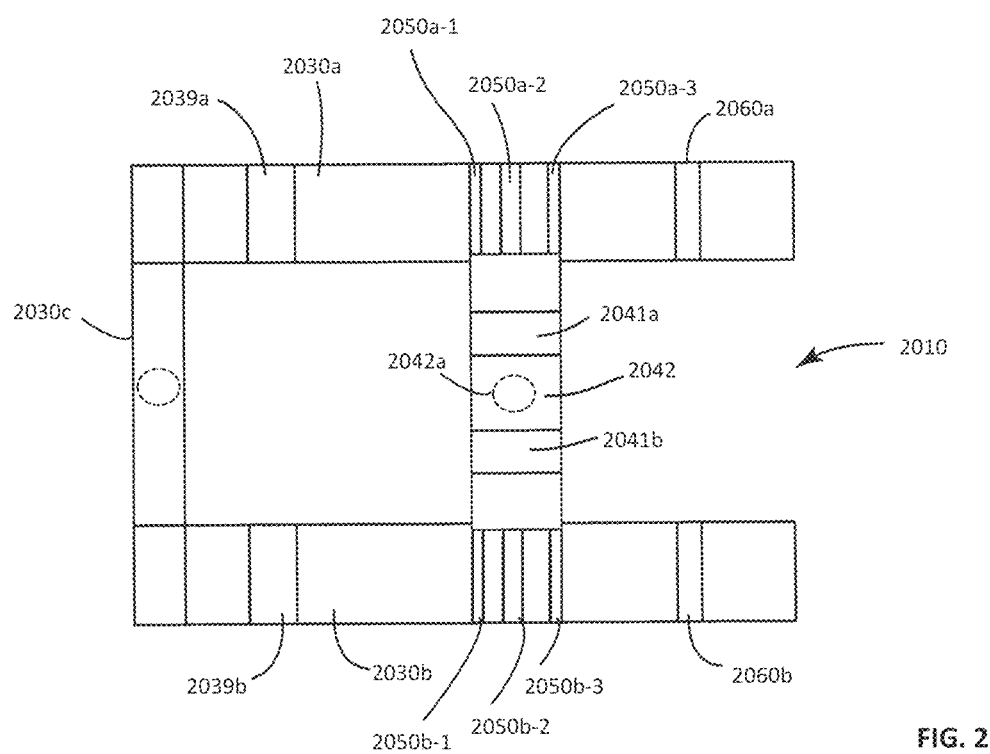
FIG. 2 is a diagram of a COVID-19 IgM/IgG multiplexed immunoassay device test cell.

FIG. 2 is a diagram of one embodiment of a COVID-19 IgM/IgG multiplexed immunoassay device test cell. The test cell 2110, as described hereinafter provides the surprising results that antibodies to multiple proteins of a single virus are detected with high sensitivity and specificity from a single blood droplet sample. More particularly, test cell 2010 includes a first sorbent strip 2030a with marker conjugate 2039a, a test zone 2050a with test lines 2050a-1, 2050a-2, 2050a-3, and control line 2060a, a second sorbent strip 2042 for receiving a sample, with the second sorbent strip optionally containing one or more separate depletion molecule zones, e.g., with depletion molecules or conjugates 2041a, 2041b on either side of a sample receiving location 2042a, a third sorbent strip 2030b with marker conjugate 2039b, a test zone 2050b with test lines 2050b-1, 2050b-2 and 2050b-3, and control line 2060b, and an optional fourth sorbent strip 2030c which is coupled to the first and third sorbent strips or integral therewith. In the embodiment of FIG. 2, test lines 2050a-1, 2050b-2 and 2050b-3 contain immobilized antigens that respectively will specifically capture the nucleocapsid protein (NP), spike protein S1 subunit (S1), and spike protein receptor binding domain (RBD) of COVID-19 virus IgM antibodies. By way of example only, the antigens may include recombinant SARS-CoV-2 (2019-nCoV) spike protein (RBD, His Tag) consisting of 234 amino acids with a predicted molecular mass of 26 kDa, a recombinant SARS-CoV-2 (2019-nCoV) nucleocapsid protein (His Tag) consisting of 430 amino acids with a predicted molecular mass of 47 kDa, and a recombinant SARS-CoV-2 (2019-nCoV) spike protein (S1 subunit, His Tag) consisting of 681 amino acids and a predicted molecular mass of 76 kDa. Similarly, test lines 2050b-1, 2050b-2 and 2050b-3 contain immobilized antigens that respectively will specifically capture the nucleocapsid protein (NP), spike protein S1 subunit (S1), and spike protein receptor binding domain (RBD) of COVID-19 virus IgG antibodies. In the embodiment of FIG. 2, marker conjugate 2039a may be a monoclonal anti-IgM (against mu-chain) gold conjugate and conjugate 2039*b* may be Protein-A Gold conjugate or a similar conjugate that will bind to the FC region of IgG antibodies.

In accord with one aspect, depletion molecules 2041*a* and 2041*b* are optional. When utilized, depletion molecules 2041*a* are conjugates for broadly depleting IgG antibodies (such as Goat anti-human IgG FC mixed with stabilizing solution containing sucrose, detergent, preservative). Similarly, when utilized, depletion molecules 2041*b* are conjugates for broadly depleting IgM antibodies. If desired, depletion molecules 2041*a* which deplete IgG antibodies could be used while depletion molecules 2041*b* for depleting IgM antibodies are not used so that the IgG test lines actually pick up both IgG and IgM antibodies, whereas the IgM test lines pick up IgM antibodies only. The conjugates may be sprayed on strip 2042 or may be immobilized thereon. In this manner, only IgM antibodies in the sample will travel from the sample receiving site 2042*a* on second sorbent strip 2042 to test zone 2050*a* (i.e., the IgG antibodies will be either trapped or will have been rendered inactive by mating with conjugate), while only IgG antibodies in the sample will travel from the sample receiving site 2042*a* to test zone 2050*b*. Whether antibodies such as Anti-human IgG or the conjugates are sprayed or immobilized, it may be useful to use white latex particles as part of the depletion conjugate.

In another embodiment, in addition or as an alternative to depletion zone 2041*a* containing conjugates for broadly depleting IgG antibodies, depletion zone 2041*a* may contain (additional) conjugates for depleting antibodies of viruses that are similar to (i.e., cross-reactive with) but different than the COVID-19 antibodies. By way of example, depletion zone 2041*a* may additionally contain antigens or conjugates that attach to Human Coronavirus HKU1, 229E, NL63, and OC43 antigens. Similarly, in addition or as an alternative to depletion zone 2041*b* containing conjugates for broadly depleting IgM antibodies, zone 2041*b* may contain (additional) antigens or conjugates for depleting e.g., Human Coronavirus HKU1, 229E, NL63, and OC43 antibodies. In this manner, the specificity of the test 2010 is increased.

The immunoassay of FIG. 2 may be utilized as follows. First, a sample (not shown) possibly containing IgG and/or IgM antibodies for COVID-19 is optionally diluted (e.g., with buffer) and provided to the second sorbent strip 2042 at 2042*a* between the depletion zones 2041*a*, 2041*b*. The sample does not immediately wet the test sites but is allowed to take time to migrate from its location of application to the depletion zones 2042*a*, 2042*b*, and then to the test sites 2050*a*, 2050*b*. If the sample is not first diluted, optionally, after providing the sample to the second sorbent strip, a measured amount of liquid such as a buffer solution may be added to the second sorbent strip to help in the migration of the sample. Regardless, if the sample includes antigens or antibodies that react with the antigens in one or both of the depletion zones, those antibodies are captured at the depletion zones and are depleted from the sample before reaching the respective test lines. To the extent that the antigens of the depletion zones are not immobilized, or loosen from the sorbent strip and travel down to the test sites, many of the reactive sites on the antibodies are occupied with depletion zone recombinant antigens so that they will not bind to the antigen at the test line. Conversely, to the extent that antibodies of interest are present in the sample, they will generally not be depleted significantly by the specific antigens in the depletion zone, but will travel down to the test line and bind to the antigens immobilized at the test lines. A sufficient time after application of the sample to the second sorbent strip of the immunoassay, a liquid such as a buffer solution is added to the first and third sorbent strips 2030*a*, 2030*b* (e.g., via the fourth sorbent strip 2030*c*). The solution is added to a location which permits it to cause the conjugates 2039*a*, 2039*b* on the first and third sorbent strips to migrate to the respective test sites (and control sites 2060*a*, 2060*b*, if provided), and to bind with the antibodies of the sample (if present) that are captured at the respective test sites. The test sites and control sites are then inspected in order to determine whether the sample is "positive" or not. Typically, a "positive" test indicating the presence of the tested antibody protein in the sample is obtained when both the test site and the control site show spots (lines) of color. A "negative" test indicating the lack of the presence of the antibody protein in the sample is obtained when only the control site shows a line of color. As with the previously described embodiments, the use of the immunoassay apparatus may be expedited by providing a housing for the sorbent strips, with the housing having holes and numbering and/or lettering to indicate that one hole in the housing is for receiving the sample (and optionally some buffer) and is to be used first, and that another hole (or holes) is for receiving the buffer solution that moves the marker conjugate and is to be used second.

It is noted that the combination of indications at the IgM test site and at the IgG test site provide a large amount of information, and that the information relating to the different specific proteins at the IgM and/or IgG test sites provides even more information. For example, since IgM antibodies are the first antibodies that the human body produced after infection, a positive or relative high signal at the IgM test site relative to the IgG test site may indicate an acute infection. A positive signal at the IgM test site in conjunction with a similar positive signal at the IgG test site may indicate an ongoing infection. A negative signal at the IgM test site and a positive signal at the IgG test site may indicate an infection that is no longer active, and possible immunity. Further, assuming that vaccinations against RBD and/or Spike protein (S1) may become available in the future for COVID-19, it is probable that a negative signal at the NP test line but a positive signal at the S1 and/or RBD test lines will indicate an effective vaccination, whereas a positive with NP antigen shows a natural infection rather than a signal caused by vaccine immunity. In fact, as discussed hereinafter, this scenario has proven to be correct.

Figure 2A:
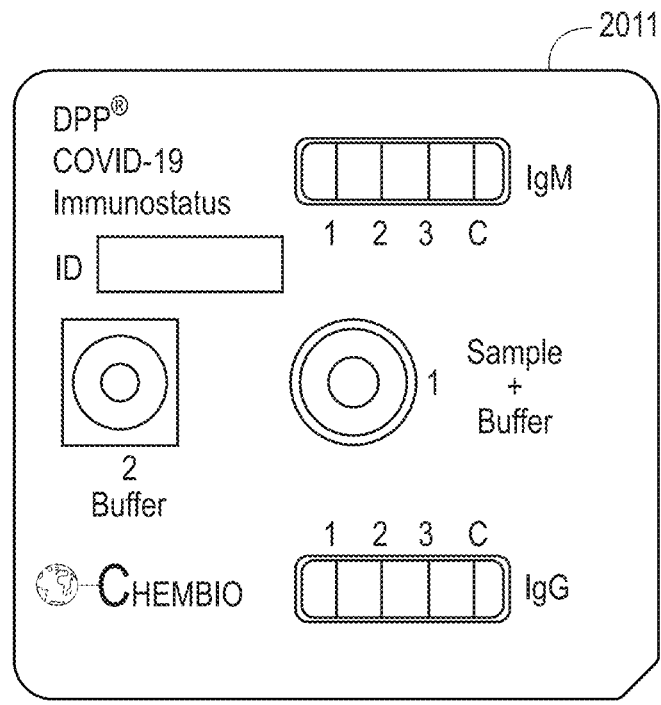
FIG. 2A is a view of a test cassette incorporating the test cell of FIG. 2.

FIG. 2A shows a test cassette 2011 that incorporates the test cell 2010 of FIG. 2. As seen, test cassette 2011 is provided with a housing having a first opening (marked 1) over the one or more sorbent strips which receive the sample (and buffer), a second opening (marked 2) over the one or more sorbent strips which receive the buffer, and third and fourth openings or windows (marked IgM and IgG) over the IgM and IgG test lines (and control lines) from which results may be seen/read.

Figure 3:
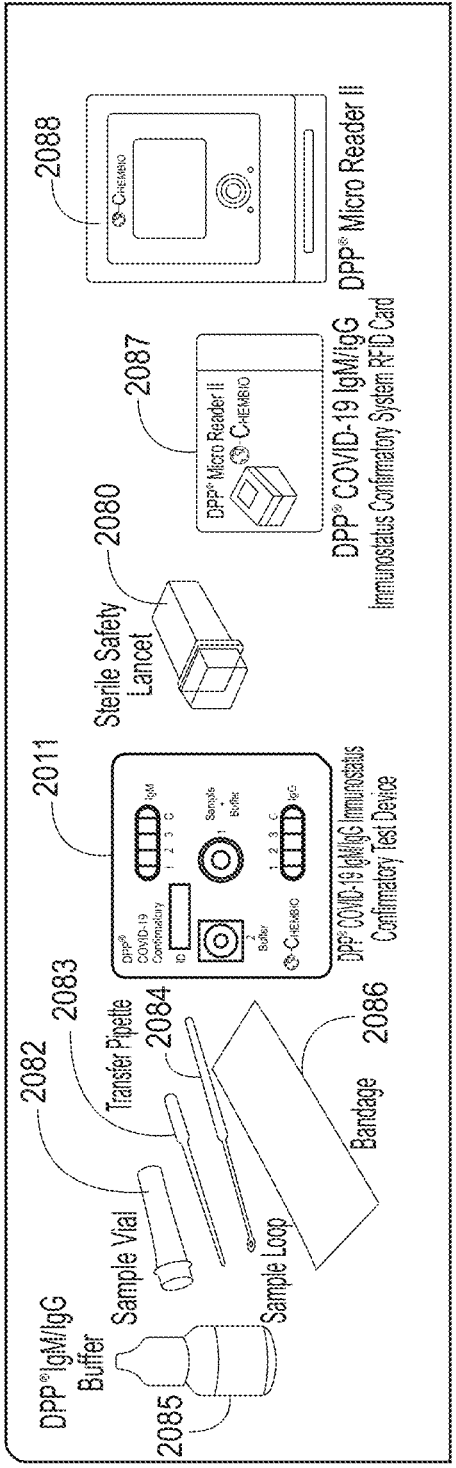
FIG. 3 is a diagram of a confirmatory test kit system utilizing the test device of FIG. 2A.

FIG. 3 is a diagram of a confirmatory test kit system utilizing the test device of FIG. 2. In particular, test kit system is shown having test device cassette 2011 containing the test device 2010, a safety lancet 2080, a sample vial 2082, a transfer pipette 2083, a sample loop 2084, a vial of buffer solution 2085, a bandage 2086, an RFID card 2087 and a test reader 2088. The reader may be a reader such as the DPP Microreader available from Chembio Diagnostics Gmbh which may provide a relative quantitative reading of test results.

Figure 4A:
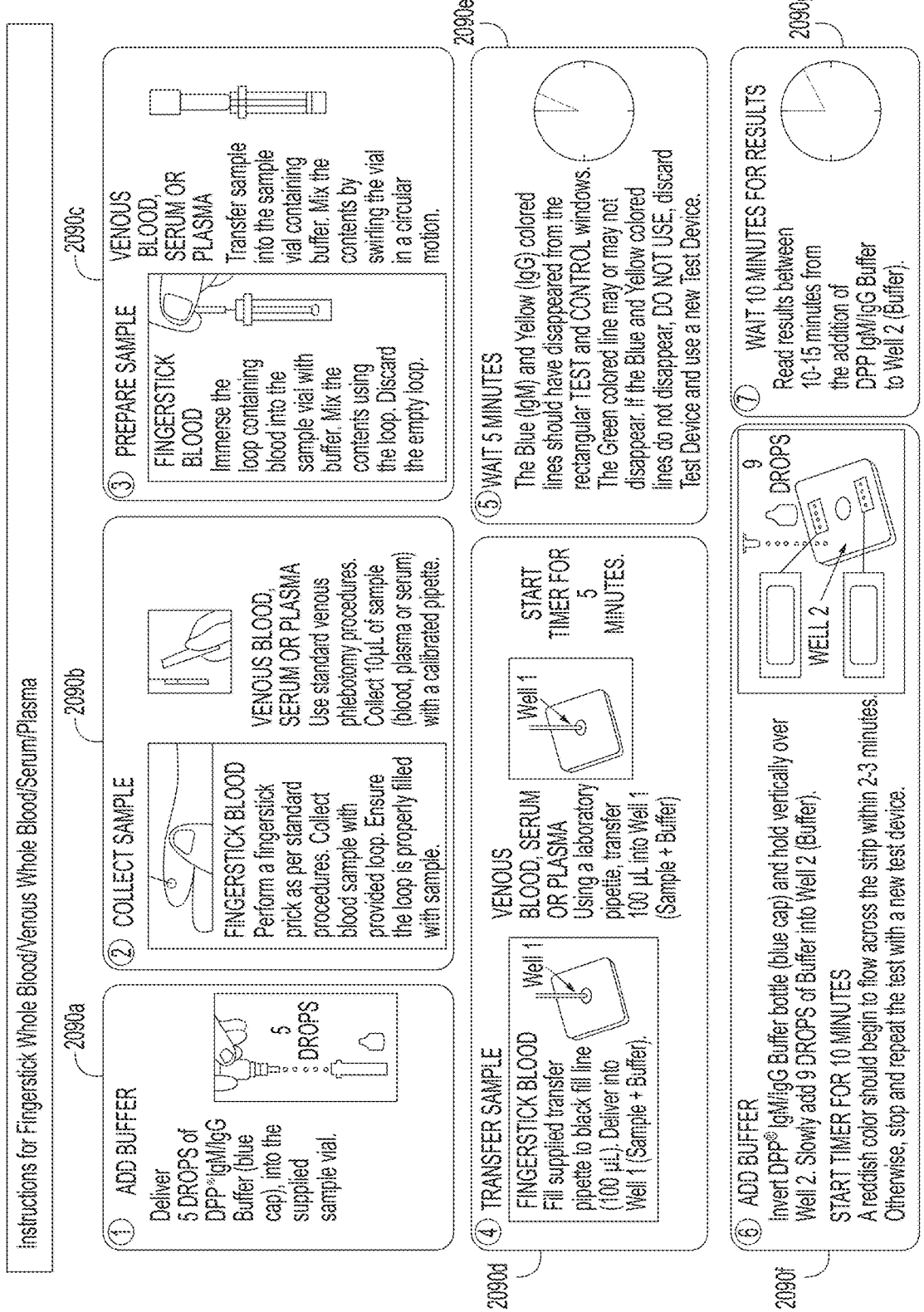
FIG. 4A is an instruction manual describing a method of using the test kit system of FIG. 3.

FIG. 4A is an instruction manual describing a method of using the test kit system of FIG. 3. At 2090*a*, five drops of buffer solution from buffer vial 2085 are supplied to the sample vial 2082. At 2090*b*, the safety lancet 2080 is used to perform a fingerstick prick per standard procedures, and the subject (patient) may be given the bandage 2086 for application on the finger. The blood sample is collected with the sample loop 2084. Standard venous phlebotomy procedures are used to collect 10 microliters of blood. At 2090c, the loop containing the blood is immersed into the sample vial with the buffer. The contents are mixed using the loop. At 2090d, the transfer pipette is filled to 100 microliters and delivered to a hole (well) in the housing of the test device cassette 2011 located over the sample site 2042a (labeled "1 Sample+Buffer). At 2090e, the user waits for approximately five minutes to see whether the colored control lines 2060a, 2060b (e.g., colored with soluble dye) lose their color (visually disappear). If so, at 2090f, approximately nine drops of buffer from buffer vial 2085 are added to a buffer well in the housing of the test device cassette 2011 located over strip 2030c (labeled "2 Buffer"). At 2090g, the user waits for approximately ten to fifteen minutes to see whether any of the test lines 2050a-1, 2050a-2, 2050a-3, 2050b-1, 2050b-2, 2050b-3 are visible. At 2090g, the control lines 2060a and 2060b may also be inspected to see whether they are now visible. If they are visible, the test results should be valid. The test results may be viewed by the user or supplied to the test reader 2088 as described with respect to FIG. 5A.

Figure 4B:
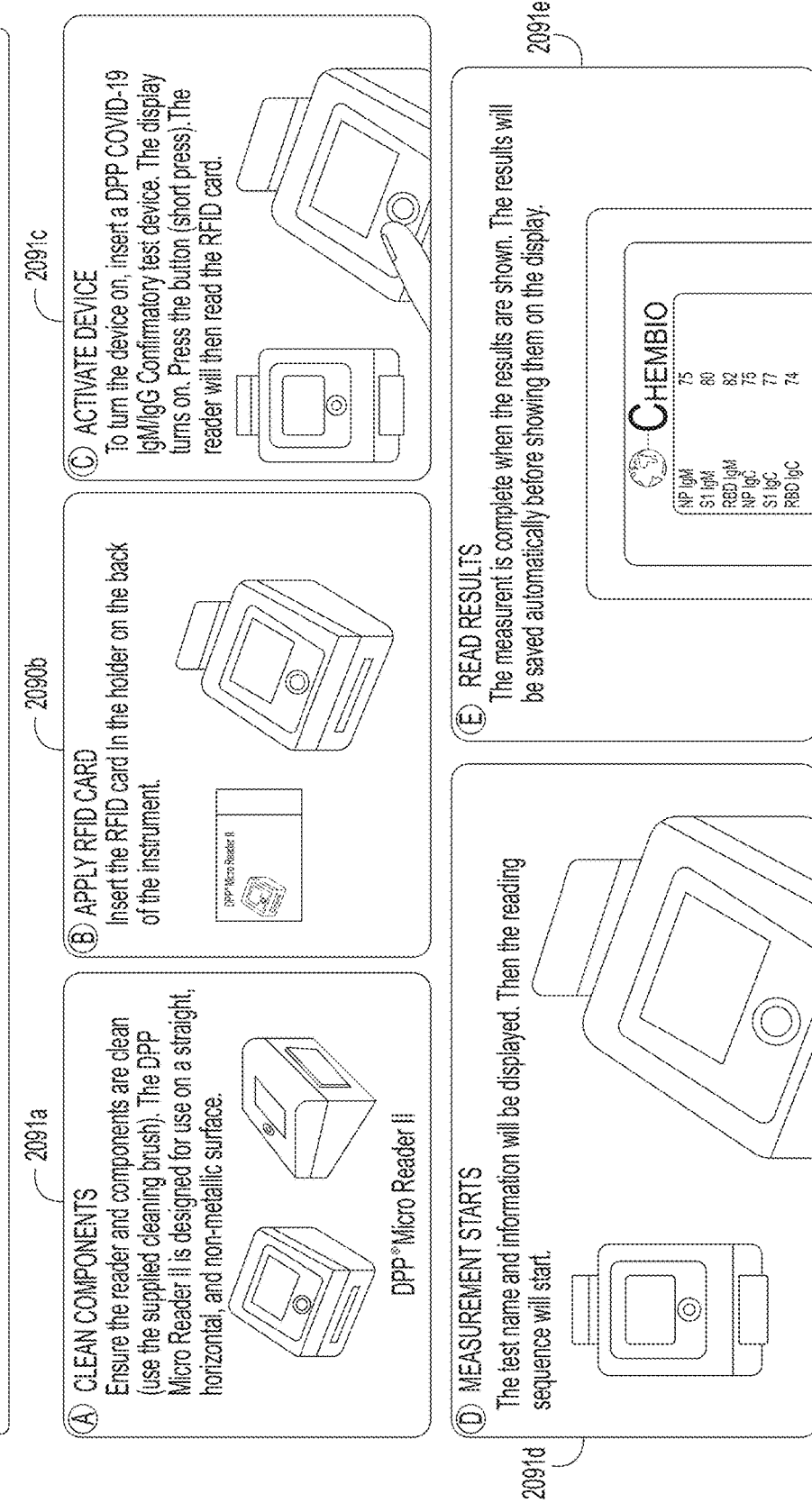
FIG. 4B is a manual showing a method of reading results from the immunoassay device of FIG. 3.

FIG. 4B is a manual showing one method of reading results from the immunoassay device of FIG. 3. FIG. 4B shows that the test reader 2088 may be cleaned at 2091a, and at 2091b, an RFID card accompanying the test device cassette 2011 may be inserted into the reader. At 2091c, the test reader is activated and the measurement/reading sequence starts at 2091d. At 2091e, the measurement is complete when the test results for each of the six test lines is shown with a relative number.

FIG. 5 is a chart of possible results provided by the reader of FIG. 3. As seen in FIG. 5, test lines 2050a-1 and 2050b-1 may show a "reactive" (positive) or "non-reactive" (negative) reading result for the COVID-19 nucleocapsid IgM and IgG proteins; test lines 2050a-2 and 2050b-2 may show a "reactive" or "non-reactive" reading result for the IgM and IgG spike protein S1 subunit; and test lines 2050a-3 and 2050b-3 may show a "reactive" or "non-reactive" reading result for the IgM and IgG spike protein receptor binding domain. The particle values displayed may be relative, and a cut-off may be selected for purposes of declaring "reactive" or "non-reactive". Thus, as shown in FIG. 36B, the cut-off value of twenty-five is selected as the minimum value for "reactive", whereas any value under twenty-five (e.g., 0 to twenty-four) is declared "unreactive".

Using the test kit of FIG. 3, including the reader, seventy-four samples that were previously subject to polymerase chain reaction (PCR) testing for COVID-19 were tested using test cells 2010 as previously described and read by reader 2088. Tables 1A and 1B below provides the readings for each of six test lines (IgM NP, S1, RBD, and IgG NP, S1, RBD). From left to right, the columns show the sample ID #, the PCR COVID-19 data results, the IgM NP, S1, and RBD results from the test cells 2010 (DPP Covid-19), the IgG NP, S1, and RBD results from the test cell 2010 (DPP Covid-19), the IgM result interpretation, the IgG interpretation, and the Total Antibody interpretation. For purposes of Tables 1A and 1B, a reader value of twenty-five or more was considered a "positive" test result, whereas a reader value of less than twenty-five was considered a "negative" test result. In the results interpretation, and IgG or IgM test was considered "positive" if any of the NP, S1 or RBD values was at twenty-five or greater, and a total antibody result was considered positive if either the IgG or IgM test result was positive. The total antibody result was considered negative only when both the IgG and IgM test results were negative. As shown in FIG. 6, which summarizes the results of Tables 1A and 1B, of the seventy-four samples obtained, fifty-six tested "positive" through PCR testing, while eighteen tested negative. The test results from the test cells 2010 adhered exactly to the PCR testing results showing that the test cells had a 100% sensitivity. It is noted that the IgG positive and negative results complied exactly with the PCR testing results, whereas the IgM results were slightly different. This result does not mean that the IgM testing was not as sensitive, as the PCR tests look for virus but does not detect antibodies. Rather, the test results using the test cells described herein provides additional and potentially valuable information. Similarly, the differences among the NP, S1, and RBD values does not necessarily reveal a lack of sensitivity. Rather, it is additional and potentially valuable information that is not provided by the PCR testing. It will be also be appreciated that the "total antibody" result provides a better sensitivity result than the result from any single protein test line. Also, in one aspect higher TgM readings relative to IgG readings may be interpreted as early infection or infection onset, whereas higher IgG readings relative to IgM readings may be interpreted as continuing or past infection as opposed to early infection or onset.

Table 1A

Summary of result for COVID-19 positive and negative samples

| | | DPP COVID-19 IgM/IgG Immunostat Confirmatory System | | | | | | | | |
|---|---|---|---|---|---|---|---|---|---|---|
| | PCR positive | NP-Rec Ag | S1-Rec Ag | RBD-Rec Ag | NP-Rec Ag | S1-Rec Ag | RBD-Rec Ag | Results Interpretation | | |
| Sample ID | COVID-19 Data | IgM Pos ≥2.5 DPP Micro Reader II Value | | | IgG Pos ≥2.5 DPP Micro Reader II Value | | | IgM | IgG | Total Antibody |
| 1 | Positive | 111 | 300 | 289 | 203 | 178 | 158 | POS | POS | POS |
| 2 | Positive | 77 | 113 | 116 | 246 | 225 | 187 | POS | POS | POS |
| 3 | Positive | 41 | 176 | 215 | 213 | 278 | 236 | POS | POS | POS |
| 4 | Positive | 149 | 101 | 213 | 297 | 112 | 148 | POS | POS | POS |
| 5 | Positive | 55 | 49 | 84 | 272 | 29 | 78 | POS | POS | POS |
| 6 | Positive | 37 | 108 | 178 | 203 | 241 | 235 | POS | POS | POS |
| 7 | Positive | 72 | 91 | 69 | 180 | 307 | 286 | POS | POS | POS |
| 8 | Positive | 70 | 151 | 184 | 117 | 267 | 251 | POS | POS | POS |
| 9 | Positive | 50 | 147 | 152 | 238 | 301 | 255 | POS | POS | POS |
| 10 | Positive | 42 | 241 | 173 | 171 | 239 | 239 | POS | POS | POS |
| 11 | Positive | 200 | 204 | 305 | 310 | 314 | 218 | POS | POS | POS |

Table 1A-continued

Summary of result for COVID-19 positive and negative samples

DPP COVID-19 IgM/IgG Immunostat Confirmatory System

| Sample ID | PCR positive COVID-19 Data | NP-Rec Ag | S1-Rec Ag | RBD-Rec Ag | NP-Rec Ag | S1-Rec Ag | RBD-Rec Ag | Results Interpretation | | |
|---|---|---|---|---|---|---|---|---|---|---|
| | | IgM Pos ≥2.5 DPP Micro Reader II Value | | | IgG Pos ≥2.5 DPP Micro Reader II Value | | | IgM | IgG | Total Antibody |
| 12 | Positive | 95 | 207 | 233 | 240 | 208 | 201 | POS | POS | POS |
| 13 | Positive | 52 | 34 | 119 | 338 | 78 | 116 | POS | POS | POS |
| 14 | Positive | 43 | 59 | 32 | 234 | 161 | 164 | POS | POS | POS |
| 15 | Positive | 33 | 73 | 159 | 203 | 95 | 169 | POS | POS | POS |
| 16 | Positive | 75 | 6 | 12 | 277 | 4 | 6 | POS | POS | POS |
| 17 | Positive | 71 | 192 | 204 | 258 | 244 | 210 | POS | POS | POS |
| 18 | Positive | 18 | 38 | 51 | 219 | 140 | 246 | POS | POS | POS |
| 19 | Positive | 159 | 86 | 75 | 104 | 238 | 249 | POS | POS | POS |
| 20 | Positive | 59 | 188 | 233 | 139 | 61 | 79 | POS | POS | POS |
| 21 | Positive | 65 | 251 | 262 | 228 | 297 | 269 | POS | POS | POS |
| 22 | Positive | 41 | 78 | 123 | 245 | 226 | 207 | POS | POS | POS |
| 23 | Positive | 71 | 3 | 7 | 289 | 3 | 2 | POS | POS | POS |
| 24 | Positive | 13 | 13 | 31 | 7 | 3 | 26 | POS | POS | POS |
| 25 | Positive | 107 | 99 | 54 | 236 | 264 | 213 | POS | POS | POS |
| R 1 | Positive | 1 | 3 | 3 | 4 | 9 | 43 | NEG | POS | POS |
| R 2 | Positive | 40 | 140 | 176 | 238 | 14 | 67 | POS | POS | POS |
| R 3 | Positive | 7 | 1 | 71 | 38 | 2 | 171 | POS | POS | POS |
| R 4 | Positive | 2 | 1 | 2 | 2 | 3 | 71 | NEG | POS | POS |
| R 5 | Positive | 24 | 13 | 25 | 194 | 9 | 98 | POS | POS | POS |
| R 6 | Positive | 0 | 1 | 63 | 5 | 2 | 163 | POS | POS | POS |
| R 7 | Positive | 2 | 2 | 6 | 28 | 27 | 45 | NEG | POS | POS |
| R 8 | Positive | 3 | 6 | 36 | 65 | 64 | 270 | POS | POS | POS |
| 189690 | positive | 21 | 22 | 88 | 16 | 38 | 51 | POS | POS | POS |
| 21230 | Positive | 13 | 5 | 17 | 140 | 10 | 12 | NEG | POS | POS |

TABLE 1B

Summary of result for COVID-19 positive and negative samples

DPP COVID-19 IgM/IgG Immunostat Confirmatory System

| Sample ID | PCR positive COVID-19 Data | NP-Rec Ag | S1-Rec Ag | RBD-Rec Ag | NP-Rec Ag | S1-Rec Ag | RBD-Rec Ag | Results Interpretation | | |
|---|---|---|---|---|---|---|---|---|---|---|
| | | IgM Pos ≥2.5 DPP Micro Reader II Value | | | IgG Pos ≥2.5 DPP Micro Reader II Value | | | IgM | IgG | Total Antibody |
| 21231 | Positive | 62 | 120 | 148 | 79 | 55 | 67 | POS | POS | POS |
| 21248 | Positive | 21 | 23 | 99 | 115 | 96 | 136 | POS | POS | POS |
| 21259 | Positive | 62 | 129 | 171 | 321 | 132 | 128 | POS | POS | POS |
| 21271 | Positive | 41 | 89 | 159 | 277 | 77 | 91 | POS | POS | POS |
| 21277 | Positive | 50 | 19 | 54 | 24 | 46 | 11 | POS | POS | POS |
| 21285 | Positive | 17 | 9 | 22 | 158 | 86 | 75 | NEG | POS | POS |
| 21287 | Positive | 100 | 39 | 144 | 254 | 16 | 29 | POS | POS | POS |
| 2000738100 | Positive | 41 | 91 | 110 | 215 | 69 | 67 | POS | POS | POS |
| 2000737900 | Positive | 29 | 4 | 6 | 184 | 93 | 50 | IND | POS | POS |
| 2000738000 | Positive | 30 | 8 | 22 | 248 | 141 | 83 | IND | POS | POS |
| 2000738200 | Positive | 12 | 5 | 4 | 26 | 10 | 5 | NEG | POS | POS |
| 2000738400 | Positive | 23 | 24 | 25 | 196 | 96 | 96 | POS | POS | POS |
| 2000738300 | Positive | 75 | 29 | 42 | 299 | 133 | 73 | POS | POS | POS |
| 2000739300 | Positive | 40 | 6 | 8 | 203 | 109 | 50 | POS | POS | POS |
| 2000739200 | Positive | 9 | 3 | 6 | 31 | 14 | 8 | NEG | POS | POS |
| 2000739600 | Positive | 42 | 8 | 28 | 222 | 8 | 6 | POS | POS | POS |
| 2000738500 | Positive | 25 | 4 | 5 | 151 | 22 | 11 | POS | POS | IND |
| 2000739500 | Positive | 35 | 90 | 78 | 238 | 88 | 72 | POS | POS | POS |
| 2000739400 | Positive | 30 | 7 | 17 | 233 | 138 | 92 | POS | POS | POS |
| 2000740800 | Positive | 53 | 23 | 31 | 308 | 167 | 118 | POS | POS | POS |
| 2000826100 | Positive | 88 | 142 | 202 | 151 | 16 | 31 | POS | POS | POS |
| 205-13 | Negative | 21 | 5 | 3 | 23 | 2 | 4 | NEG | NEG | NEG |

TABLE 1B-continued

Summary of result for COVID-19 positive and negative samples

| | | \multicolumn{6}{c}{DPP COVID-19 IgM/IgG Immunostat Confirmatory System} | | | |
| | PCR positive | NP-Rec Ag | S1-Rec Ag | RBD-Rec Ag | NP-Rec Ag | S1-Rec Ag | RBD-Rec Ag | \multicolumn{3}{c}{Results Interpretation} |
| Sample ID | COVID-19 Data | \multicolumn{3}{c}{IgM Pos ≥2.5 DPP Micro Reader II Value} | \multicolumn{3}{c}{IgG Pos ≥2.5 DPP Micro Reader II Value} | IgM | IgG | Total Antibody |
|---|---|---|---|---|---|---|---|---|---|---|
| 05-0394 | Negative | 3 | 1 | 3 | 3 | 16 | 1 | NEG | NEG | NEG |
| 04-0142 | Negative | 23 | 5 | 2 | 7 | 3 | 3 | NEG | NEG | NEG |
| 04-0113 | Negative | 9 | 2 | 2 | 4 | 7 | 3 | NEG | NEG | NEG |
| 01-0106 | Negative | 11 | 4 | 4 | 4 | 4 | 2 | NEG | NEG | NEG |
| 20779 | Negative | 8 | 9 | 3 | 6 | 2 | 3 | NEG | NEG | NEG |
| 20959 | Negative | 6 | 2 | 4 | 5 | 3 | 2 | NEG | NEG | NEG |
| 21115 | Negative | 7 | 3 | 2 | 11 | 2 | 3 | NEG | NEG | NEG |
| 21184 | Negative | 5 | 2 | 3 | 9 | 2 | 2 | NEG | NEG | NEG |
| 21187 | Negative | 16 | 1 | 2 | 9 | 1 | 2 | NEG | NEG | NEG |
| R288286 | Negative | 3 | 3 | 1 | 4 | 4 | 1 | NEG | NEG | NEG |
| R288292 | Negative | 8 | 4 | 1 | 2 | 2 | 1 | NEG | NEG | NEG |
| R288305 | Negative | 9 | 2 | 1 | 3 | 1 | 6 | NEG | NEG | NEG |
| R288307 | Negative | 7 | 4 | 1 | 3 | 2 | 2 | NEG | NEG | NEG |
| R288309 | Negative | 5 | 2 | 1 | 9 | 1 | 8 | NEG | NEG | NEG |
| R288316 | Negative | 9 | 4 | 1 | 5 | 2 | 7 | NEG | NEG | NEG |
| R288322 | Negative | 6 | 4 | 3 | 4 | 2 | 9 | NEG | NEG | NEG |
| R294175 | Negative | 8 | 4 | 2 | 10 | 1 | 8 | NEG | NEG | NEG |

It will be appreciated that in various embodiments, instead of utilizing three separate test lines for testing three different proteins of a single virus such as COVID-19, only two separate test lines may be used for testing different proteins of the virus. By way of example, the test lines may be arranged to test for just the NP and RDB proteins of COVID-19. Similarly, instead of using two or three separate lines for testing two or three different proteins of a single virus, four or more lines for testing for or more different proteins of the same virus may be used. Thus, by way of example only, four lines for testing the NP, S1, S2 and RBD proteins of the COVID-19 virus antibodies may be utilized.

According to additional embodiments, rather than testing for the presence of both IgG and IgM antibodies to multiple proteins of a single virus, a test may just test for the IgG or IgM antibodies to the multiple proteins of the single virus. Alternatively, the test may test for multiple of IgG, IgM, IgA antibodies to the multiple proteins of the single virus in any combination; e.g., IgG and IgM, IgG and IgA, IgM and IgA, IgG, IgM and IgA.

Figure 7:
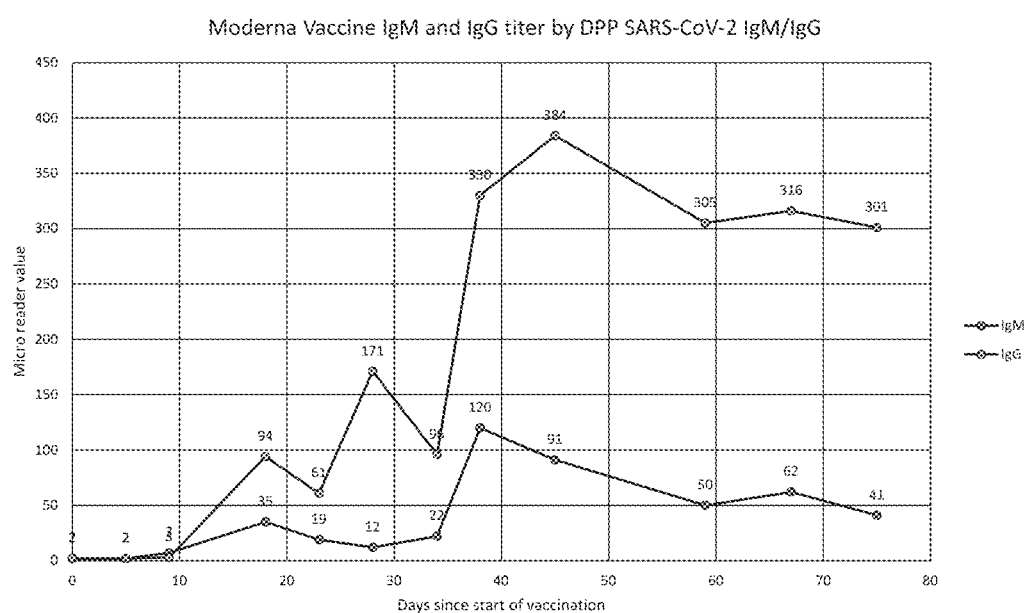
FIG. 7 is a graph of IgM RBD and IgG RBD antibody readings using the test kit system of FIG. 3 versus days since vaccination for a subject vaccinated with a Moderna SARS-Cov-2 Vaccine.

As previously mentioned, various valuable results may be obtained from a test device such as previously described that is capable of simultaneously determining the presence of two or more antibodies to a single virus. In the case of the COVID-19 virus, and in according to aspects, blood samples are taken from a healthy subject over a period of approximately ten weeks, starting from a sample taken immediately before vaccination (inoculation) with the Moderna spike-based vaccine. The blood samples are applied to a test cassette 2011 such as shown in FIG. 2 according to the instructions of FIGS. 3 and 4A read by a reader 2088 according to the instructions of FIG. 4b. RBD, NP, and S1 IgG and IgM values are determined. Prior to vaccination, single digit values are obtained for all test results (IgG RBD, IgG NP, IgG S1, IgM RBD, IgM NP, and IgM S1). As seen in FIG. 7 which shows reader values for IgG and IgM RBD antibody values over a seventy-five day period, the readings over the first ten days were in the single digits (with values under twenty-five considered "negative"), and by day eighteen had increased to values of thirty-five and ninety-four for IgM and IgG RBD respectively. A second vaccination shot is administered at day twenty-eight, and antibody values for both IgM RBD and IgG RBD increase significantly through day thirty-eight for the IgM and day forty-five for the IgG. Thereafter, values decrease somewhat and generally plateau, but remain at a level of showing a positive test result. During this seventy-five day period, both the IgG NP and IgM NP results continue to read in the single digits, and the IgG S1 results remain track the RBD results, except that the numbers are slightly lower, and during the end of the period, the IgM S1 drops below the twenty-five value threshold, so that IgM S1 reads negative.

Figure 8:
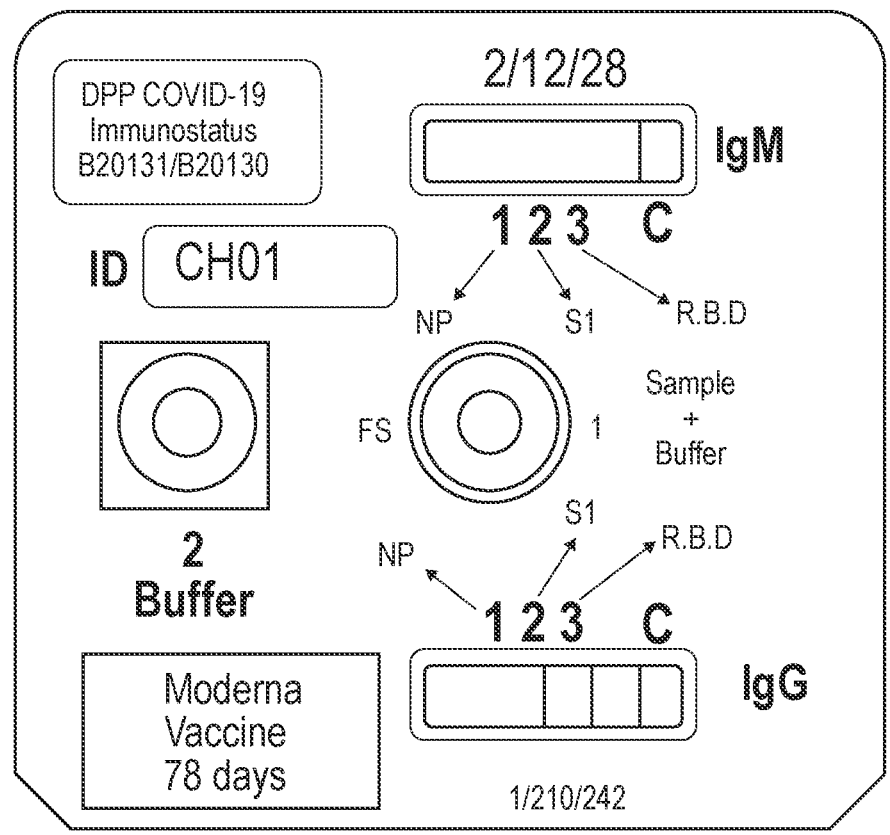
FIG. 8 is a test cell of FIG. 2A marked with reading values for IgM and IgG antibodies of a COVID-19 virus as determined by a reader of FIG. 3.

A test cassette such as shown in FIG. 2 to which a blood sample from the subject is applied at day seventy-eight is shown in FIG. 8. It shows values of two, twelve and twenty-eight for IgM NP, IgM S1 and IgM RBD respectively, and values of one, two hundred ten, and two hundred forty-two for IgG NP, IgG S1 and IgG RBD respectively.

Meanwhile, starting at seven weeks, oral fluid, nasal wall swab mucus from one or both nostrils, and nasopharyngeal mucus of a subject are obtained from the subject as well and likewise tested for IgG RBD and IgM RBD, resulting in IgG RBD levels similar to the blood sample results, but with IgM RBD values in single digits which is well below the blood sample results.

From the above, various valuable and surprising results may be obtained. By way of example, and as previously posited, a positive reading of IgG RBD and/or IgM RBD antibody results combined with a negative reading of IgG NP or IgM NP results is indicative of effective vaccination without infection, whereas a positive reading of NP along with positive reading of RBD indicates an ongoing COVID-19 infection. In this manner, and according to methods, it is possible to distinguish between whether a vaccinated individual is presently infected or not. If a vaccinated individual is infected, appropriate action such as treatment and/or quarantining may be implemented. Further, by way of example, in vaccinated individuals, the IgG RBD values are substantially higher than the IgM RBD values and it may be useful to test and consider only IgG values in vaccinated individuals to see whether the individual is effectively vaccinated, has a present infection, or neither. Further yet, by way of example, blood, nasal wall mucus (from nostrils), nasopharyngeal and saliva tests all appear to show similar results, and therefore, in various methods it may be possible to monitor post-vaccinated patients regularly over a long period of time (months and years) through nasal wall swabs (or saliva, blood samples, or nasopharyngeal) using the provided immunoassays and readers to see whether a booster shot is advised. In particular, in one embodiment, a booster shot is considered advisable if the IgG RBD and/or IgG S1 value drops below a threshold value (e.g., twenty-five for the reader) which would otherwise represent a positive immune response. In another embodiment, a booster shot is considered advisable if the IgG RBD and/or IgG S1 value drops by a predetermined factor (e.g., a factor of ten) from the highest value recorded for that individual.

There have been described and illustrated herein several embodiments of immunoassays and methods of their use. While particular embodiments have been described, it is not intended that the invention be limited thereto, as it is intended that the invention be as broad in scope as the art will allow and that the specification be read likewise. Thus, while the specification discusses ligand binding using antigen/antibody reactions, other ligand binding mechanisms such as aptamer binding, nucleic acid binding, enzymatic binding, etc. may also be used. Also, while specific test-line antigens, marker conjugates, and depletion antigens and conjugates have been described, other antigens, marker conjugates, and depletion antigens and conjugates could be utilized. Further, while the test cells are described as having two test lines for testing for two ligands of a single virus, three test lines for testing for three ligands of a single virus, and six test lines for testing six ligands of a single virus, it will be appreciated that different numbers of lines may be utilized for testing for different numbers of ligands. Further yet, while particular housing arrangements for sorbent strips are described, it will be appreciated that the housing could have different shapes, have different numbers of holes, and the sorbent strips may be laid out differently.

Those skilled in the art will also appreciate that the housing may be modified in additional ways to include separate windows for each test line. Also, while embodiments were described in conjunction with the use of a buffer solution which is added to the migration path of the conjugate and optionally to the migration path of the sample, it will be appreciated that one or more buffers may be chosen as desired to be added to the migration paths depending upon the test or tests to be conducted. Thus, buffers such as phosphate buffers or TRIS (tris hydroxymethylaminomethane) buffers are often utilized. However, the disclosure is intended to encompass the use of any diluent including water. In addition, the diluent may, if needed, may be added to and mixed with the sample prior to adding the sample to the sorbent material or the sample may be deposited first and the diluent may be added thereafter. Likewise, any diluent capable of causing conjugate to migrate may be utilized, and may be premixed with the conjugate in a liquid conjugate system, or provided to the migration path for the conjugate in a dry conjugate system. It will therefore be appreciated by those skilled in the art that yet other modifications could be made without deviating from its spirit and scope of the claims.

What is claimed is:

1. A test device for determining presence of at least two different antibodies to a COVID-19 (Severe acute respiratory syndrome coronavirus-2) virus in a liquid sample, comprising:

a first test zone configured to detect presence of the at least two different antibodies to the COVID-19 virus;

a first sorbent strip having a first location for receiving a solution and defining a first migration path leading to the first test zone for the solution, wherein the first sorbent strip contains a first marker conjugate adapted to move with the solution along said first migration path and bind to said at least two different antibodies to the COVID-19 virus; and a second sorbent strip distinct from said first sorbent strip and having a second location for receiving the liquid sample and defining a second migration path leading to the first test zone for the liquid sample, said first and second sorbent strips touching each other at said first test zone;

wherein the first test zone has first and second test sites located on or in at least one of said first sorbent strip and said second sorbent strip, said first test site having an immobilized first ligand binding mechanism that binds to antibodies to a first protein of the COVID-19 virus and said second test site having an immobilized second ligand binding mechanism that binds to antibodies to a second protein of the COVID-19 virus, wherein said second location is removed from said first and second test sites such that the liquid sample applied to said second location requires time to migrate to said first and second test sites and does not immediately wet said first and second test sites.

2. The test device according to claim 1, wherein the test device determines the presence of at least three different antibodies to the COVID-19 virus and the first test zone includes a third test site located on or in one at least one of said first sorbent strip and said second sorbent strip adjacent the second test site, said third test site having an immobilized third ligand binding mechanism that binds to antibodies to a third protein of the COVID-19 virus.

3. The test device according to claim 1, wherein the immobilized first and second ligand binding mechanisms of said first and second test sites include antigens that bind to IgG antibodies to a nucleocapsid protein (NP) and a spike protein receptor binding domain (RBD) of the COVID-19 virus.

4. The test device according to claim 1, wherein the immobilized first and second ligand binding mechanisms of said first and second test sites include antigens that bind to IgM antibodies to a nucleocapsid protein (NP) and spike protein receptor binding domain (RBD) of the COVID-19 virus.

5. The test device according to claim 2, wherein the immobilized first, second, and third ligand binding mechanisms of said first, second, and third test sites include antigens that bind to IgG antibodies to a nucleocapsid protein (NP) and a spike protein S1 subunit (S1) and a spike protein receptor binding domain (RBD) of the COVID-19 virus.

6. The test device according to claim 2, wherein the immobilized first, second, and third ligand binding mechanisms of said first, second, and third test sites include antigens that bind to IgM antibodies to a nucleocapsid protein (NP) and a spike protein S1 subunit (S1) and a spike protein receptor binding domain (RBD) of the COVID-19 virus.

7. The test device according to claim 1, further comprising a third sorbent strip which receives the solution and defines a third migration path leading to a second test zone for the solution, wherein the third sorbent strip contains a second marker conjugate different than said first marker conjugate, the second marker conjugate adapted to move with the solution along said third migration path and bind to antibodies to the COVID-19 virus, wherein the second sorbent strip touches the third sorbent strip at the second test zone, and wherein the second test zone has a plurality of additional test sites with different immobilized ligand binding mechanisms that bind to antibodies to different proteins of the COVID-19 virus.

8. The test device according to claim 7, wherein the immobilized first and second ligand binding mechanisms of said first test zone includes antigens that bind to IgG antibodies to a nucleocapsid protein (NP) and a spike protein receptor binding domain (RBD) of the COVID-19 virus and the different immobilized ligand mechanisms of the additional test sites of the second test zone includes antigens that bind to IgM antibodies to a nucleocapsid protein (NP) and a spike protein receptor binding domain (RBD) of the COVID-19 virus.

9. The test device according to claim 7, wherein the test device determines the presence of at least three different antibodies to the COVID-19 virus and the first test zone includes a third test site located on or in one at least one of said first sorbent strip and said second sorbent strip adjacent the second test site, said third test site having an immobilized third ligand binding mechanism that binds to antibodies to a third protein of the COVID-19 virus, and wherein the immobilized first, second, and third ligand binding mechanisms of the first, second and third test sites of said first test zone includes antigens that bind to IgG antibodies to a nucleocapsid protein (NP) and a spike protein S1 subunit (S1) and a spike protein receptor binding domain (RBD) of the COVID-19 virus, and the different immobilized ligand binding mechanisms of the additional test sites of the second test zone includes antigens that bind to IgM antibodies to a nucleocapsid protein (NP) and a spike protein S1 subunit (S1) and a spike protein receptor binding domain (RBD) of the COVID-19 virus.

10. The test device according to claim 1, wherein the second sorbent strip includes a depletion zone located between said second location and said first test zone, wherein said depletion zone has depletion molecules or conjugates for broadly depleting one of COVID-19 virus IgG antibodies and COVID-19 virus IgM antibodies.

11. The test device according to claim 1, wherein the second sorbent strip includes a depletion zone located between said second location and said first test zone, wherein said depletion zone has depletion molecules or conjugate comprising antigens or conjugates for depleting Human Coronavirus HKU1, 229E, NL63, and OC43 antibodies.

12. The test device according to claim 1, wherein the first test zone includes a third test site located on or in one at least one of said first sorbent strip and said second sorbent strip adjacent the second test site and a fourth test site located on or in one at least one of said first sorbent strip and said second sorbent strip adjacent the third test site, said third test site having an immobilized third ligand binding mechanism that binds to antibodies to a third protein of the COVID-19 virus, and the fourth test site having an immobilized fourth ligand binding mechanism that binds to antibodies to a fourth protein of the COVID-19 virus, wherein said first, second, third and fourth ligand binding mechanisms include antigens that bind to IgG antibodies or IgM antibodies to a nucleocapsid protein (NP) and a spike protein S1 subunit (S1) and a spike protein S2 subunit (S2) and a spike protein receptor binding domain (RBD) of the COVID-19 virus.

13. The test device according to claim 1, wherein the immobilized first and second ligand binding mechanisms of said first test zone include antigens that capture a plurality of COVID-19 IgG antibodies or COVID-19 IgM antibodies.

14. The test device according to claim 13, wherein the antigens of said first test site include antigens selected from recombinant nucleocapsid proteins (NP), recombinant spike protein receptor binding domains (RBD), recombinant spike proteins (S1), and combinations thereof, and wherein the antigens of said second test site include antigens selected from recombinant nucleocapsid proteins (NP), recombinant spike protein receptor binding domains (RBD), and recombinant spike proteins (S1), and combinations thereof.

15. The test device according to claim 1, wherein the first marker conjugate comprises a monoclonal anti-IgM gold conjugate or a Protein-A Gold conjugate.

* * * * *